United States Patent
Deuel et al.

(10) Patent No.: US 12,023,020 B2
(45) Date of Patent: Jul. 2, 2024

(54) SUTURE CINCHING AND CUTTING DEVICE

(71) Applicant: BOSTON SCIENTIFIC SCIMED, INC., Maple Grove, MN (US)

(72) Inventors: Christopher R. Deuel, Melrose, MA (US); Ryan V. Wales, Northborough, MA (US); Sean P. Fleury, Minneapolis, MN (US); Stan Robert Gilbert, Litchfield, NH (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 662 days.

(21) Appl. No.: 17/089,634

(22) Filed: Nov. 4, 2020

(65) Prior Publication Data

US 2021/0128139 A1   May 6, 2021

Related U.S. Application Data

(60) Provisional application No. 62/930,723, filed on Nov. 5, 2019.

(51) Int. Cl.
*A61B 17/04* (2006.01)
(52) U.S. Cl.
CPC ...... *A61B 17/0467* (2013.01); *A61B 2560/04* (2013.01)
(58) Field of Classification Search
CPC ...... A61B 17/0467; A61B 2017/00477; A61B 2017/0496; A61B 2560/04
USPC ........................................................ 606/144
See application file for complete search history.

(56) References Cited

U.S. PATENT DOCUMENTS

| | | | |
|---|---|---|---|
| 7,993,368 B2 | 8/2011 | Gambale et al. |
| 8,444,673 B2 | 5/2013 | Thielen et al. |
| 8,540,735 B2 | 9/2013 | Mitelberg et al. |
| 8,974,371 B2 | 3/2015 | Durgin et al. |
| 9,486,192 B2 | 11/2016 | Pipenhagen |
| 9,788,831 B2 | 10/2017 | Mitelberg |
| 10,426,457 B2 | 10/2019 | Mitelberg et al. |
| 2011/0196388 A1 | 8/2011 | Thielen et al. |
| 2012/0158023 A1 | 6/2012 | Mitelberg et al. |
| 2012/0259346 A1 | 10/2012 | Hansen et al. |
| 2018/0028180 A1 | 2/2018 | Binmoeller et al. |
| 2019/0357899 A1 | 11/2019 | Gilbert et al. |
| 2020/0178956 A1 | 6/2020 | Mitelberg et al. |

FOREIGN PATENT DOCUMENTS

WO   2019226891 A1   11/2019

OTHER PUBLICATIONS

International Search Report and Written Opinion dated Jan. 13, 2021 for International Application No. PCT/US2020/058975.
Invitation to Pay Additional Fees dated Jan. 14, 2021 for International Application No. PCT/US2020/058976.

*Primary Examiner* — Kankindi Rwego
(74) *Attorney, Agent, or Firm* — Seager, Tufte & Wickhem, LLP

(57) ABSTRACT

Medical devices for applying a cinch to one or more suture and cutting the suture, and methods for making and using such devices are disclosed. An example medical device may include an elongated shaft, a connection sleeve, a cinch sleeve coupled to the connection sleeve, and a cinch member. An elongated inner shaft may extend through and be longitudinally movable within the elongated shaft, connection sleeve, cinch sleeve, and cinch member.

16 Claims, 13 Drawing Sheets

SUTURE CINCHING AND CUTTING DEVICE

CROSS REFERENCE TO RELATED APPLICATIONS

The present application claims the benefit of and priority to U.S. Provisional Patent Application Ser. No. 62/930,723, filed on Nov. 5, 2019, titled SUTURE CINCHING AND CUTTING DEVICE, the disclosure of which is incorporated herein by reference.

TECHNICAL FIELD

The present disclosure pertains to medical devices, and methods for manufacturing medical devices. More particularly, the present disclosure pertains to devices for cinching and cutting a suture, and methods for manufacturing and using such devices.

BACKGROUND

A wide variety of medical devices and methods have been developed for suturing tissue, and securing and/or terminating the free end of a suture relative to the tissue once a suture is in place. These devices are manufactured by any one of a variety of different manufacturing methods and may be used according to any one of a variety of methods. Of the known devices and methods, each has certain advantages and disadvantages. There is an ongoing need to provide alternative devices as well as alternative methods for manufacturing and using such devices.

SUMMARY

This disclosure provides design, material, manufacturing method, and use alternatives for suture termination devices, for example, devices for applying a cinch to a suture. In an example, a medical device for applying a cinch to one or more suture comprises an elongated shaft defining a shaft lumen, a connection sleeve having a sleeve lumen and at least one connector, a cinch sleeve defining a cinch lumen and having a proximal portion with at least one proximal coupling member configured to releasably engage at least one connector of the connection sleeve, the cinch sleeve having a distal position in which the proximal portion is disposed within the sleeve lumen and the at least one proximal coupling member is engaged with the at least one connector of the connection sleeve, a cinch member defining a cinch member lumen, the cinch member including at least a proximal segment configured to fit within the cinch lumen, and an elongated inner shaft extending through and longitudinally movable within the shaft lumen, the sleeve lumen, the cinch lumen, and the cinch member lumen.

Alternatively or additionally to any of the above examples, the medical device further comprises a coupler connected to the elongated shaft, the coupler having a coupler lumen and a distal coupling member, wherein the at least one connector includes first and second connectors, wherein the first connector is configured to releasably engage the distal coupling member.

Alternatively or additionally to any of the above examples, the at least one proximal coupling member is releasably engaged with the second connector.

Alternatively or additionally to any of the above examples, the sleeve lumen has a sleeve lumen diameter, the cinch sleeve having an outer surface defining a shoulder, the shoulder having a proximally facing shoulder surface and having a shoulder diameter greater than the sleeve lumen diameter, wherein the proximal portion of the cinch sleeve extends proximal of the shoulder.

Alternatively or additionally to any of the above examples, when the cinch sleeve is in the distal position, a gap is defined between the proximally facing shoulder surface and a distally facing end surface of the connection sleeve.

Alternatively or additionally to any of the above examples, the medical device further comprises an opening through the outer surface of the cinch sleeve into the cinch lumen, and at least one suture cutting element disposed on one or both of the connection sleeve and the opening, and wherein proximal movement of the cinch sleeve from the distal position to a proximal position engages the at least one suture cutting element for cutting one or more suture extending through the opening.

Alternatively or additionally to any of the above examples, when the cinch sleeve moves toward the proximal position, the proximal coupling member disengages from the second connector of the connection sleeve and moves proximally, releasing the distal coupling member of the coupler from the first connector of the connection sleeve.

Alternatively or additionally to any of the above examples, a distal end section of the elongated inner shaft is configured to releasably engage the cinch member lumen, wherein proximal longitudinal movement of the elongated inner shaft moves the cinch member from a first configuration in which at least a part of the cinch member is spaced apart from a distal end of the cinch sleeve, to a second configuration in which the cinch member engages the cinch lumen.

Alternatively or additionally to any of the above examples, from the second configuration, further proximal longitudinal movement of the elongated inner shaft moves the cinch sleeve proximally such that the proximal coupling member is engaged with the first connector of the connection sleeve, and the distal coupling member of the coupler is disengaged from the connection sleeve, resulting in a third configuration.

Alternatively or additionally to any of the above examples, further proximal longitudinal movement of the elongated inner shaft moves the coupled cinch member and cinch sleeve from the third configuration to a fourth configuration in which a cinch assembly including the cinch member, cinch sleeve, and connection sleeve is separated from a shaft assembly including the elongated shaft and coupler.

Alternatively or additionally to any of the above examples, the cinch member lumen has a distal section and a proximal section, wherein a diameter of the distal section is larger than a diameter of the proximal section, wherein the elongated inner shaft includes a distal region having a diameter larger than the diameter of the proximal section of the cinch member lumen, wherein the distal region is compressible such that application of a predetermined amount of proximal longitudinal force compresses the distal region, allowing it to move into the proximal section of the cinch member lumen.

Alternatively or additionally to any of the above examples, the first and second connectors are first and second apertures, and the distal and proximal coupling members include proximal and distal prongs configured to removably engage the first and second apertures.

Alternatively or additionally to any of the above examples, the sleeve lumen has a sleeve lumen diameter, the cinch sleeve having an outer surface defining a shoulder, the shoulder having a proximally facing shoulder surface and having a shoulder diameter greater than the sleeve lumen diameter, wherein the proximal portion of the cinch sleeve extends proximal of the shoulder, wherein when the cinch sleeve is in the distal position, a gap is defined between the proximally facing shoulder surface and a distally facing end surface of the connection sleeve.

Alternatively or additionally to any of the above examples, the medical device further comprises an opening through the outer surface of the cinch sleeve into the cinch lumen, and at least one suture cutting element disposed on one or both of the connection sleeve and the opening, and wherein proximal movement of the cinch sleeve from the distal position to a proximal position engages the at least one suture cutting element for cutting one or more suture extending through the opening.

Alternatively or additionally to any of the above examples, when the cinch sleeve moves from the distal position to the proximal position, the proximal coupling member disengages from the at least one connector of the connection sleeve, releasing the connection sleeve from the cinch sleeve.

Alternatively or additionally to any of the above examples, a distal end section of the elongated inner shaft is configured to releasably engage the cinch member lumen, wherein proximal longitudinal movement of the elongated inner shaft moves the cinch member from a first configuration in which at least a part of the cinch member is spaced apart from a distal end of the cinch sleeve, to a second configuration in which the cinch member engages the cinch lumen.

Alternatively or additionally to any of the above examples, as the cinch member moves from the first configuration to the second configuration, a distal end of the cinch member moves the proximal coupling member out of engagement with the at least one connector on the connection sleeve.

Alternatively or additionally to any of the above examples, further proximal longitudinal movement of the elongated inner shaft moves the coupled cinch member and cinch sleeve from the second configuration to a third configuration in which a cinch assembly including the cinch member, cinch sleeve, and connection sleeve is separated from a shaft assembly including the elongated shaft and coupler.

In another example, a medical device for applying a cinch to one or more suture comprises an elongated shaft defining a shaft lumen, a connection sleeve having a sleeve lumen and first and second opposing deflectable arms, each deflectable arm having a distal prong extending into the sleeve lumen, a cinch sleeve defining a cinch lumen and having a proximal portion with an opening extending into the cinch lumen and first and second opposing apertures configured to releasably engage the first and second deflectable arms, a cinch member defining a cinch member lumen, the cinch member including at least a proximal portion configured to fit within the cinch lumen, and an elongated inner shaft extending through and longitudinally movable within the shaft lumen, the sleeve lumen, the cinch lumen, and the cinch member lumen, wherein the medical device has a first configuration in which the proximal portion of the cinch sleeve is disposed within the sleeve lumen and the prongs are engaged with the first and second apertures, and at least some of the proximal portion of the cinch member is spaced apart from a distal end of the cinch sleeve, wherein the medical device has a second configuration in which an entirety of the proximal portion of the cinch member resides within the cinch lumen, an entirety of the proximal portion of the cinch sleeve resides within the sleeve lumen, and the prongs are disengaged with the first and second apertures.

In another example, a method of securing and cutting one or more suture comprises inserting one or more suture into a distal end of a cinch sleeve, through a portion of a lumen thereof, and out an opening in a wall of a proximal portion of the cinch sleeve, wherein the proximal portion is disposed within a sleeve lumen of a connection sleeve with the opening positioned distal of a distal end of the connection sleeve, the connection sleeve releasably engaged with the proximal portion of the cinch sleeve, wherein a cutting surface is defined on at least one of the opening and the distal end of the connection sleeve, inserting a cinch member into the lumen of the cinch sleeve, the cinch member configured to engage the lumen of the cinch sleeve in a friction fit, thereby coupling the cinch member and cinch sleeve and securing the one or more suture between the cinch member and an inner surface of the lumen of the cinch sleeve, and cutting the one or more suture by moving the cinch sleeve with coupled cinch member proximally within the sleeve lumen, wherein moving the opening in the cinch sleeve into the sleeve lumen engages the cutting surface to cut the one or more suture.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
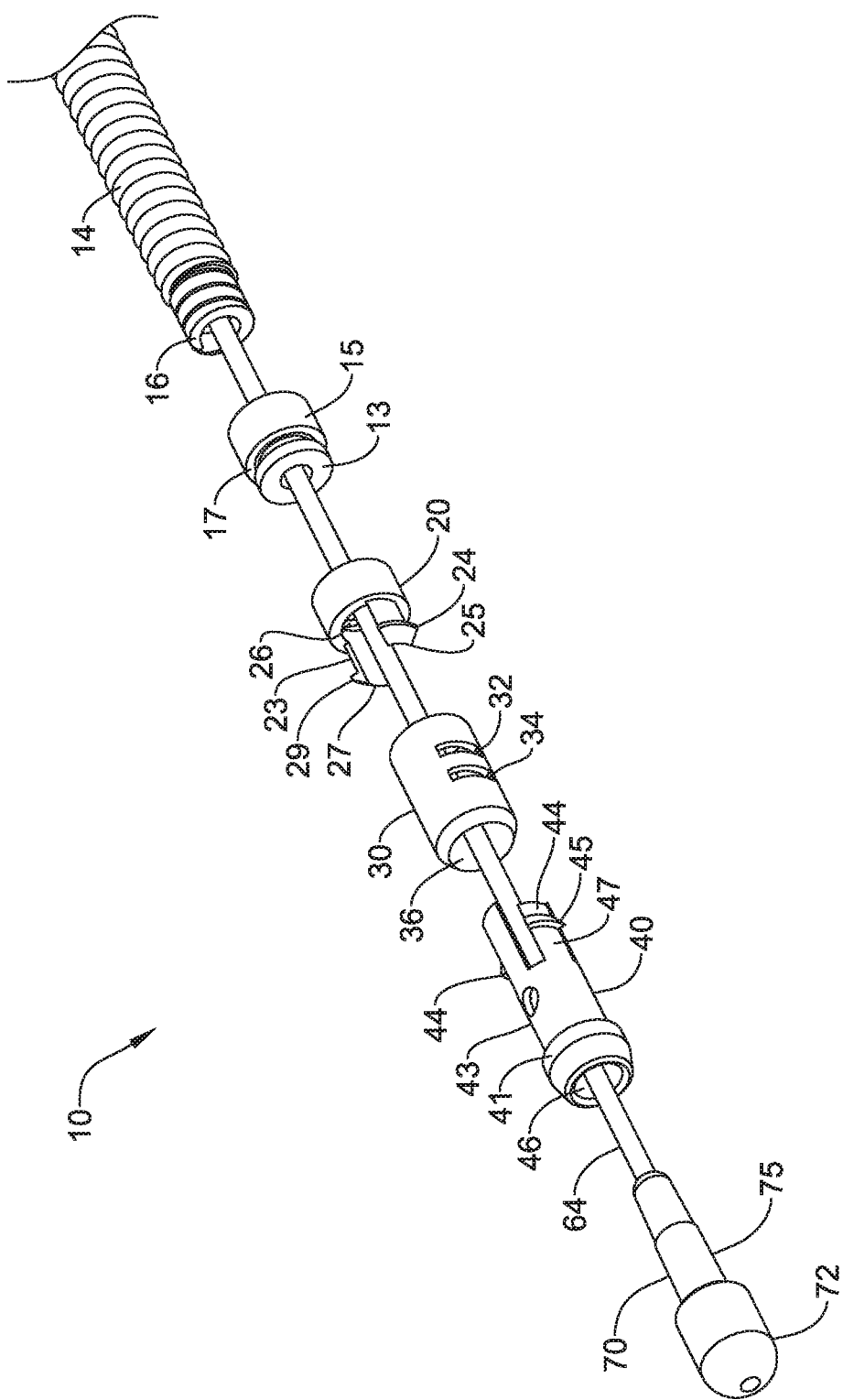
FIG. 1 is a perspective exploded view of a portion of an example medical device for applying a cinch to a suture.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used in connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Medical suturing is used in a number of different interventions. Some of the interventions may include endoscopic suturing at remote sites within the patient and/or otherwise at sites that may be challenging to access. When the suturing process is complete, it may be desirable to terminate the suture in a way that maintains the suture so that the suture does not easily come undone. This may include using a device such as a cinch in order to maintain the suture. Disclosed herein are medical devices that may be used to secure and cut the suture. The medical devices disclosed herein may be delivered through the working channel of an endoscope. At least some of these devices utilize a cinch to maintain the suture. Some example remote sites in which the medical devices disclosed herein may be utilized include, without limitation, the gastro-intestinal (GI) tract, including the stomach, esophagus, and intestines, and within the heart including the heart valves and chambers. Some example procedures in which the devices may be used include, without limitation, gastric bypass, closure of perforations, full thickness resections, closure of post endoscopic submucosal dissection (ESD) sites, gastro jejunal anastomosis and lower esophageal sphincter (LES) repair, stent fixation, bariatric revision and closure of defects, and heart valve repair and replacement. Some additional details of such devices are disclosed herein.

FIG. 1 shows a partial exploded view of a medical device 10 for applying a cinch to a suture, showing some of the components of the medical device 10. The medical device 10 may include an elongated shaft 14 having a shaft lumen 16 and including a cap 15, a coupler 20 having a coupler lumen 26, a connection sleeve 30 having a sleeve lumen 36, a cinch sleeve 40 having a cinch lumen 46, and a cinch member 70 having a cinch member lumen 76 (see FIG. 3). An elongated inner shaft 64 may extend through and be longitudinally movable through the shaft lumen 16, coupler lumen 26, sleeve lumen 36, cinch lumen 46, and cinch member lumen 76. The elongated inner shaft 64 may be a solid wire, coil, or ribbon, or may be a generally tubular member defining a lumen along a part or the entire length thereof, or a combination of these structures.

The elongated shaft 14 may include and/or be made of an elongated tubular member defining the shaft lumen 16. In the embodiment shown, the elongated shaft 14 is a coiled tubular shaft, however, other configurations are contemplated. For example, the elongated shaft 14 may be a solid metallic or polymer tubular member, a tubular member including and/or made of and/or reinforced with a coil, braid and/or mesh material, or the like. Further, the elongated shaft 14 may include one or more slots and/or grooves and/or channels formed therein, for example, to enhance the flexibility characteristics thereof. The elongated shaft 14 may include or be made of one or more metals, polymers, and/or composite or layered or reinforced structures thereof, including any of those disclosed herein.

In some examples, the elongated shaft 14 may include a cap 15 attached to the distal end of the elongated shaft 14. The cap 15 may be attached to the elongated shaft 14 by threading, adhesive, welding, soldering, or other suitable connection method. The cap 15 may include a distal connection element for connecting to the coupler 20. In the example shown in FIGS. 1-6, the cap 15 includes a groove 17 adjacent the distal end 13 of the cap 15. As shown in FIG. 3, the coupler 20 may include a projection 22 configured to fit into the groove 17 to secure the coupler 20 to the cap 15. In some examples, the elongated shaft 14 does not include the cap 15 and the coupler 20 is attached directly to the elongated shaft 14, with a threaded engagement, adhesive, weld, solder, or other suitable connection. The coupler 20 may include a distal coupling member 24. In the example shown in FIGS. 1-6, the distal coupling member 24 includes two deflectable arms 23 each having a prong 25 at the distal end. Each prong may have a distal point 27 and a flank 29 extending outward from the distal point 27. Although two deflectable arms 23 positioned on opposing sides of the coupler 20 are illustrated in FIGS. 1-6, it is understood that the distal coupling member 24 may include any number of deflectable arms 23, e.g., three, four, five, six, and the deflectable arms 23 may be located at any position around the coupler 20.

The connection sleeve 30 may include a first and second connectors. In the example shown in FIGS. 1-6, the first connector includes a pair of first apertures 32 and the second connector includes a pair of second apertures 34, corresponding with the two deflectable arms 23 of the distal coupling member 24. The connection sleeve 30 may include any number of connectors, e.g., two, three, four, five, six, corresponding with the number of deflectable arms 23 making up the distal coupling member 24. The connectors will be aligned to accept the deflectable arms 23 The cinch sleeve 40 has an outer surface that may define a shoulder 41 with a proximally facing shoulder surface 42 and having a shoulder diameter D1 greater than the diameter of the sleeve lumen 36, as shown in FIG. 3. In the embodiment shown, shoulder 41 is defined by a generally stepped portion having a rapid and/or stepped increase in outer diameter. However, in other embodiments, the outer surface of the cinch sleeve 40 may be tapered and/or angled gradually and/or in a stepwise fashion such that the outer diameter increases in size from the proximal portion 43 to the shoulder 41 in a distal direction in a more gradual manner, and the shoulder 41 may be more subtle. In such embodiments, the widened diameter portion and/or shoulder 41 may simply be defined by a first part along the outer surface that includes an outer diameter sized such that it cannot fit into the sleeve lumen 36. Such embodiments will still include a proximally facing shoulder surface 42, in that the angle and/or taper would still provide a surface that is facing in a proximal direction in a tapered and/or angled manner.

The cinch sleeve 40 may include a proximal portion 43 extending proximal of the shoulder 41, and the proximal portion 43 may include a proximal coupling member 44 configured to releasably engage first the second aperture 34 and then the first aperture 32 of the connection sleeve 30. In the example shown in FIGS. 1-6, the proximal coupling member 44 includes two deflectable arms 47 each having a prong 45 at the proximal end. The cinch sleeve 40 may define an opening 49 in a sidewall of the proximal portion 43. the opening 49 provides an exit for a suture 5 disposed within the cinch lumen 46 of the cinch sleeve 40.

Figure 2:
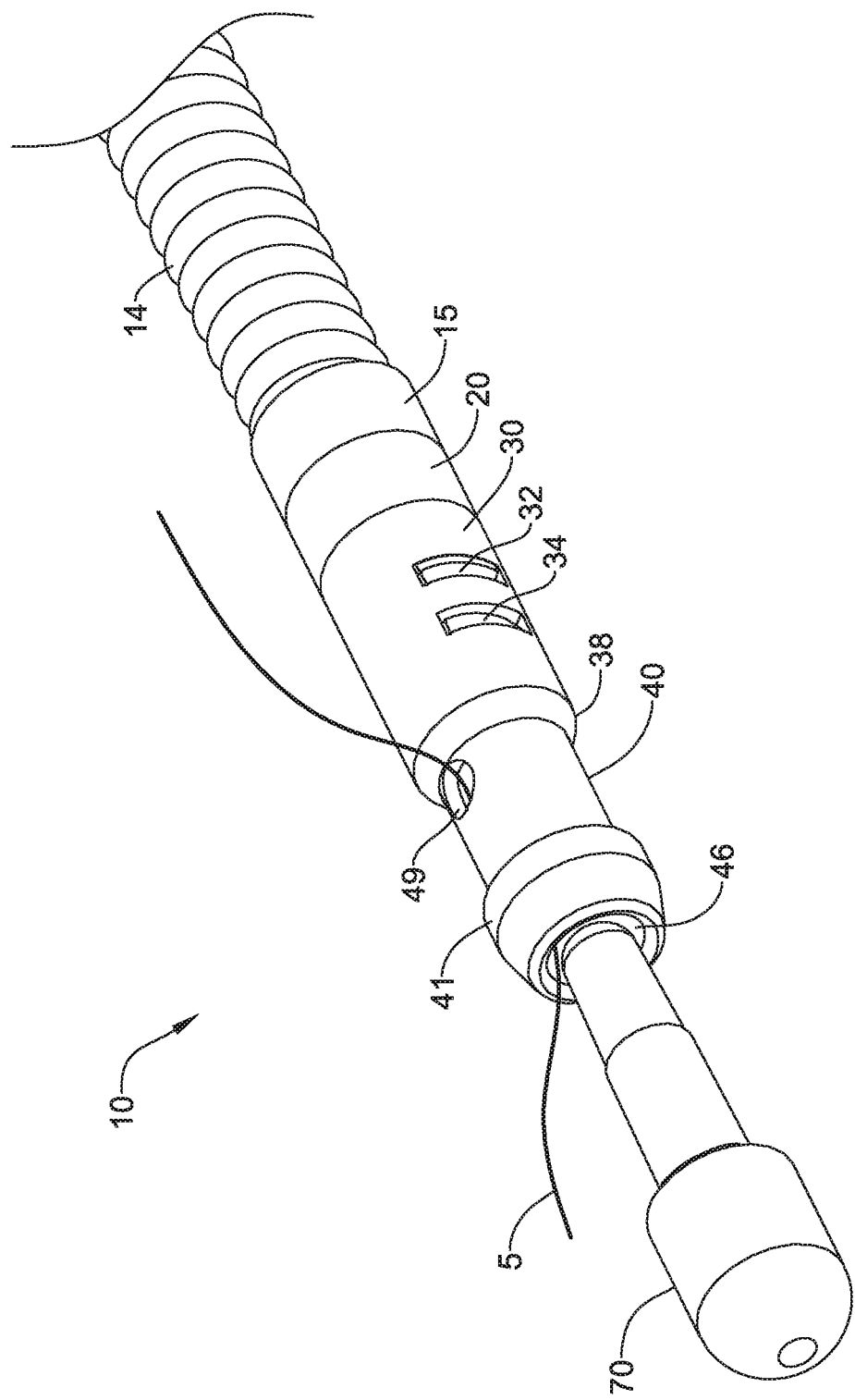
FIG. 2 is a perspective view of the medical device as shown in FIG. 1, in a first configuration.
Figure 3:
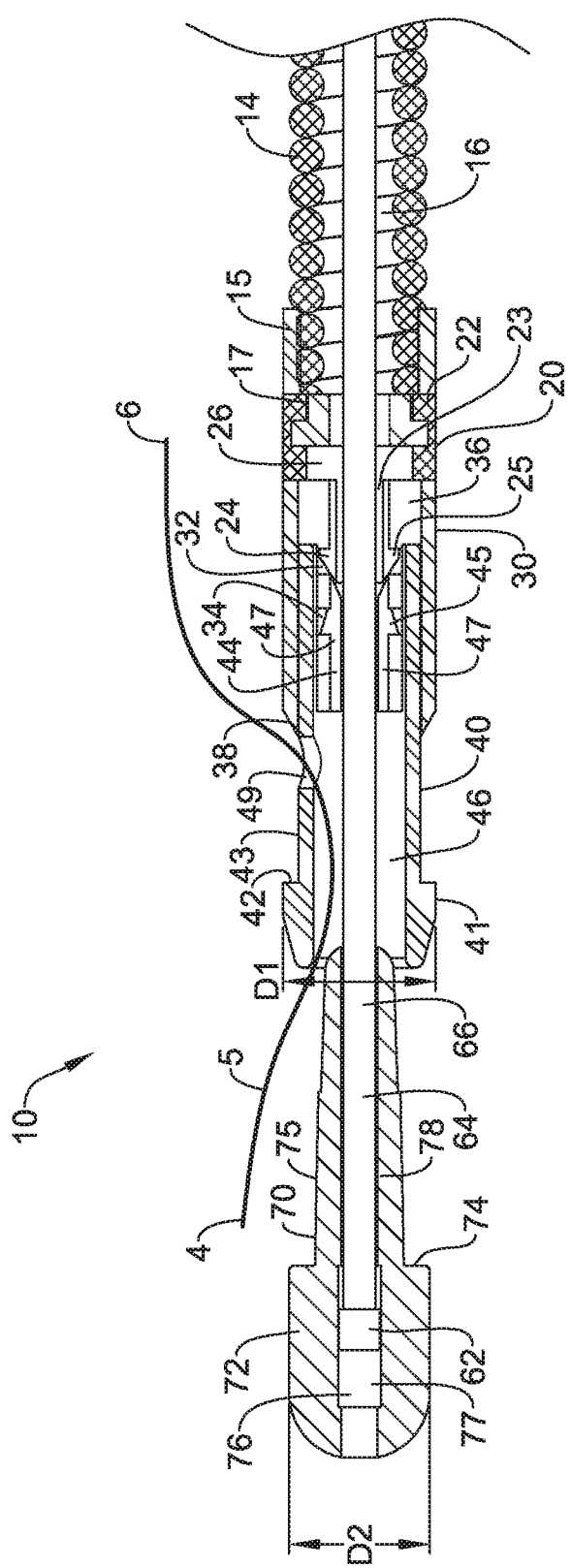
FIG. 3 is a side cross-sectional view of the medical device as shown in FIG. 1, in the first configuration.

In a first configuration, shown in FIG. 2, the elongated shaft 14, cap 15 if present, coupler 20, connection sleeve 30, and cinch sleeve 40 are all connected, with the cinch member 70 extended distally away from the cinch sleeve 40. In this configuration, a suture 5 may be inserted into the distal end of the cinch sleeve 40 and out through the opening 49 in the sidewall.

The cinch member 70 may be configured to engage the cinch sleeve 40 to secure the suture 5. The cinch member 70 may include a distal head 72 with a diameter D2 greater than the diameter of the cinch lumen 46, as shown in FIG. 3. The distal head 72 may have a proximally facing shoulder surface 74. The transition between the diameters of the distal head 72 and a proximal portion 75 may occur rapidly, defining a generally stepped shoulder portion having a rapid and/or stepped increase in outer diameter, as shown in FIG. 3. However, in other embodiments, the transition in diameters may be tapered and/or angled gradually and/or in a stepwise fashion such that the outer diameter increases in size in a distal direction in a more gradual manner, and a more subtle shoulder may be defined. In such embodiments, the widened diameter portion and/or shoulder may simply be defined by a distal head 72 that includes an outer diameter sized such that it cannot fit into the cinch lumen 46 of the cinch sleeve 40.

The cinch member 70 may have a proximal portion 75 configured to at least partially fit within the cinch lumen 46 in a friction fit. The cinch lumen 46 may have a tapered or constant inner diameter. The proximal portion 75 is configured and/or designed to mate with the cinch lumen 46 to trap and/or wedge a portion of a suture 5 therebetween. As such, the cinch member 70, in combination with the cinch sleeve 40, make up the "cinch" that will be applied to the suture. The cinch member 70 may have a cinch member lumen 76 extending at least partially therethrough. The cinch member lumen 76 may have a distal section 77 and a proximal section 78. The diameter of the distal section 77 may be larger than the diameter of the proximal section 78. In the example shown in FIGS. 1-6, the cinch member lumen 76 extends completely through the cinch member 70, however, this is not necessary. In some examples, the cinch member lumen 76 may extend only through the proximal portion 75, with the distal head 72 being solid and devoid of any lumen. In this embodiment, the distal end of the inner shaft 64 may be bonded to the lumen 76 with a frangible bond that may be broken by a predetermined proximal force once the cinch member 70 is pulled into the cinch sleeve 50.

The elongated inner shaft 64 may include a distal region 62 and a proximal region 66. The distal region 62 and proximal region 66 may be a single monolithic piece, or the distal region 62 may be a separate element that is connected to the proximal region 66. The distal region 62 may be sized to engage the cinch member lumen 76. The diameter of the distal region 62 may be larger than the diameter of the proximal region 66. The diameter of the distal region 62 may be slightly larger than the proximal section 78 of the cinch member lumen 76 to provide an interference fit. In some examples, the distal region 62 may be compressible or deformable such that the application of a predetermined amount of proximal longitudinal force allows the interference fit to be overcome, thereby allowing the enlarged distal region 62 to be pulled through the narrower proximal section 78 of the cinch member lumen 76. In other examples, the distal region 62 may be rigid and the lumen 78 may be deformable to allow the distal region 62 to be pulled proximally through the cinch member 70. In the first configuration, the distal region 62 of the elongated inner shaft 64 may be disposed within the distal section 77 of the cinch member lumen 76 and the proximal region 66 is disposed within the proximal section 78 of the cinch member lumen 76, as shown in FIG. 3.

FIGS. 2-6 illustrate the steps involved in securing and cutting a suture using the medical device 10. The medical device 10 is assembled into a deployment or first configuration shown in FIGS. 2 and 3. The elongated shaft 14, cap 15 if present, coupler 20, connection sleeve 30, and cinch sleeve 40 are all connected and the elongated inner shaft 64 is disposed within the cinch member lumen 76 and extends through the shaft lumen 16, coupler lumen 26, sleeve lumen 36, and cinch lumen 46, with the cinch member 70 disposed distal of the cinch sleeve 40, as shown in FIGS. 2 and 3.

The first apertures 32 may be configured to receive the prongs 25 on the coupler 20. In other examples, the first connector may be an inwardly extending projection configured to engage the distal coupling member 24. As the coupler 20 and connection sleeve 30 are moved into contact, the deflectable arms 23 are deflected inward into the coupler lumen 26. The deflectable arms 23 move along the sleeve lumen 36 until the prongs 25 reach the first apertures 32 at which point the deflectable arms 23 move outward and the prongs 25 are inserted into the apertures, thereby securing the coupler 20 to the connection sleeve 30.

During assembly, as the cinch sleeve 40 and connection sleeve 30 are moved into contact, the deflectable arms 47 are deflected inward into the cinch lumen 46. The deflectable arms 47 move along the sleeve lumen 36 until the prongs 45 reach the second apertures 34 at which point the deflectable arms 47 move outward and the prongs 45 are inserted into the apertures, thereby securing the cinch sleeve 40 to the connection sleeve 30. The prongs 45 are configured such that further movement proximally of the cinch sleeve 40 deflects the prongs 45 inward, releasing them from the second apertures 34 and moving then toward the first apertures 32. When the prongs 45 reach the first apertures 32, the deflectable arms 47 may move outward, and the prongs 45 may engage the first apertures 32.

In the first configuration, the cinch sleeve may be in a distal position in which the proximal portion 43 of the cinch sleeve 40 is disposed within the sleeve lumen 36 and the prongs 45 of the proximal coupling member 44 are engaged with the second apertures 34 of the connection sleeve 30 and a gap is defined between the proximally facing shoulder surface 42 and a distally facing end surface 38 of the connection sleeve 30, leaving the opening 49 exposed and providing space for the suture 5 to be threaded through the cinch lumen 46 and out the opening, as shown in FIG. 3. The proximal coupling member 44 may be configured to releasably engage the second aperture 34 on the connection sleeve 30 and then the first aperture 32. In the example shown in FIGS. 1-6, the second apertures 34 are configured to receive the prongs 45 on the cinch sleeve 40. In other examples, the second connector may be an inwardly extending projection configured to engage the proximal coupling member 44.

The device 10 may be loaded with a suture 5 and be used to apply a cinch to the suture 5. For example, following a suturing procedure in which a first end 4 of the suture 5 is disposed within the tissue, the second, or free end 6 of the suture 5 may be loaded into and/or through the device 10. The proximal end of the suture may be fed into the distal end of the device 10 and along the appropriate pathway through the device 10. This may be done with or without using a tool or guide, such as a tubular guide, wire, loop, needle, or the like.

The free end 6 may be passed into the cinch lumen 46 of the cinch sleeve 40 and out through an opening 49 in the proximal portion 43 of the cinch sleeve 40 that is disposed distal of the connection sleeve 30 in the first configuration shown in FIGS. 2 and 3. In the example shown in FIGS. 2 and 3, the entire cinch member 70 is positioned distal of the cinch sleeve 40. In other examples, the distal head 72 and at least part of the proximal portion of the cinch member 70 are positioned distal of the distal end of the cinch sleeve 40 such that sufficient space exists between the proximal portion 75 of the cinch member 70 and the inner surface of the cinch lumen 46 to thread the suture 5 through the bore to the opening 49.

Figure 4:
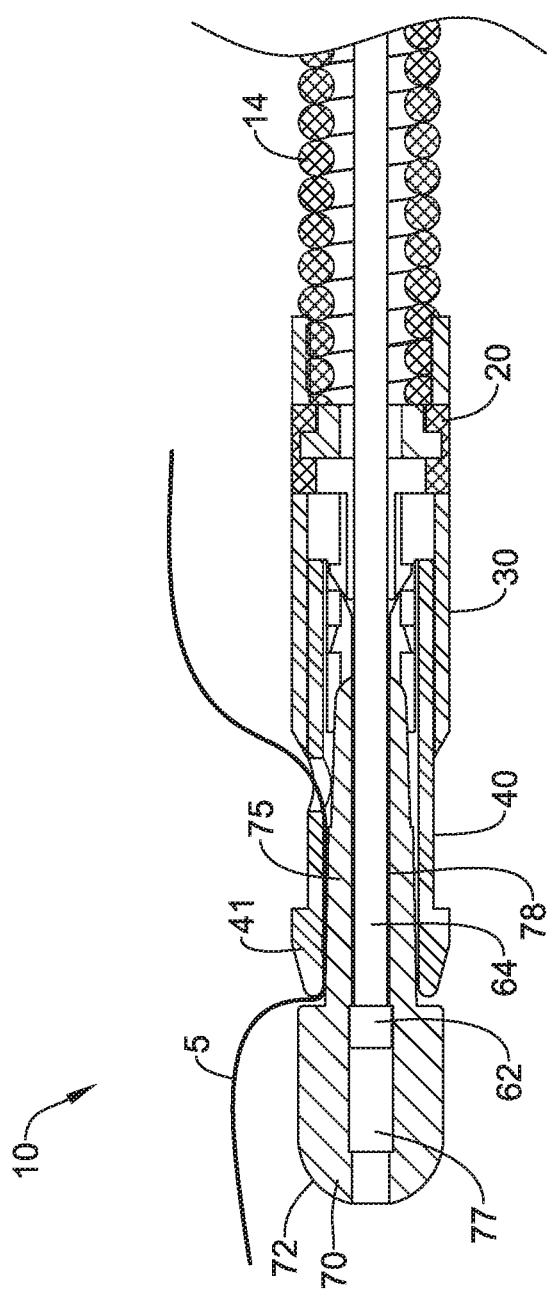
FIG. 4 is a side cross-sectional view of the medical device as shown in FIG. 1, in a second configuration.

Once the suture 5 is disposed within the cinch lumen 46 of the cinch sleeve 40, the suture 5 may be secured by moving the cinch member 70 into the cinch lumen 46 of the cinch sleeve 40. This may be achieved by pulling the inner shaft 64 proximally. A first stage of proximal longitudinal movement of the elongated inner shaft 64 pulls the engaged cinch member 70 into the cinch lumen 46 of the cinch sleeve 40 until the proximal portion 75 of the cinch member 70 engages the inner surface of the cinch sleeve 50, thereby compressing and securing the suture 5, moving the device 100 into a second configuration as shown in FIG. 4. The interference fit between the proximal portion 75 and the inner surface of the cinch lumen 56 secures the suture 5 even when there is a gap between the proximally facing shoulder surface 74 and the distal end 58 of the cinch sleeve 50. This gap may prevent crimping and possible damage to the suture as it bends at an approximately right angle. However, in other examples, the cinch member 70 may be pulled proximally until the proximally facing shoulder surface 74 engages the distal end 58 of the cinch sleeve 50, thereby providing an additional securement point. In such an example, the edges of the proximally facing shoulder surface 74 and the distal end 58 of the cinch sleeve 50 are generally smooth to prevent damage to the suture. In some examples, the cinch sleeve 40 may remain in substantially the same distal position in both the first and second configurations, with only the cinch member 70 and elongated inner shaft 64 moving proximally.

Figure 5:
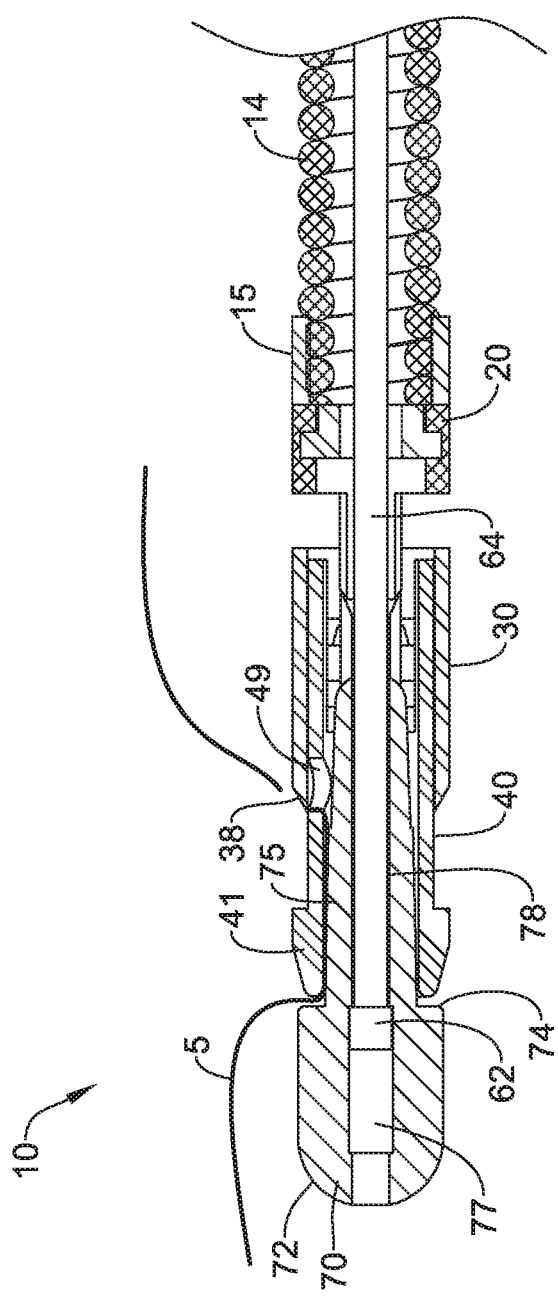
FIG. 5 is a side cross-sectional view of the medical device as shown in FIG. 1, in a third configuration.

In a second stage of proximal longitudinal movement, the elongated inner shaft 64 may then be pulled further proximally, pulling the attached cinch member 70 and engaged cinch sleeve 40 further into the connection sleeve 30, moving the cinch sleeve into a third configuration, as shown in FIG. 5. A cutting surface or shear edge may be defined on one or both of the distally facing end surface 38 of the connection sleeve 30 and the opening 49 in the cinch sleeve 40. Moving the cinch sleeve 40 further into the connection sleeve 30 moves the opening 49 under the distally facing end surface 38, moving the suture 5 against the cutting surface and cutting the suture 5, as shown in FIG. 5. The second stage of proximal longitudinal movement of the elongated inner shaft 64 may further move the proximally facing shoulder surface 42 of the cinch sleeve 40 into contact with the distally facing end surface 38 of the connection sleeve 30.

When the coupler 20 is engaged with the connection sleeve 30 as discussed above, movement of the cinch sleeve 40 from the second configuration to the third configuration releases the prongs 45 from the second apertures 34 and causes the prongs 45 to exert a proximal force on the prongs 25 of the coupler 20. The prongs 25 are configured such that a force applied proximally to the distal point 27 of the prongs 25 and along the flank 29 of the prongs 25 deflects the prongs 25 inward, releasing them from the first apertures 32, and pushes the coupler 20 proximally away from the connection sleeve 30, as shown in FIG. 5. Once the prongs 25 of the coupler 20 are moved out of the first apertures 32, allowing the coupler 20 to be disengaged from the connection sleeve 30, the cinch sleeve 40 may move into a proximal position, with the prongs 45 engaged with the first apertures 32, placing the device 100 in a third configuration, as shown in FIG. 5.

Once the coupler 20 has been disengaged from the connection sleeve 30, a third stage of proximal longitudinal movement of the elongated inner shaft 64 may move the cinch sleeve 40 further proximally, releasing the prongs 45 from the first apertures 32. This proximal movement of the inner shaft 64 may expand the deformable proximal section 78 of the cinch member lumen 76 as the rigid distal region 62 moves proximally, allowing the inner shaft 64 to move completely through and out of the cinch member lumen 76, disengaging the inner shaft 64 from the cinch member 70.

Figure 6:
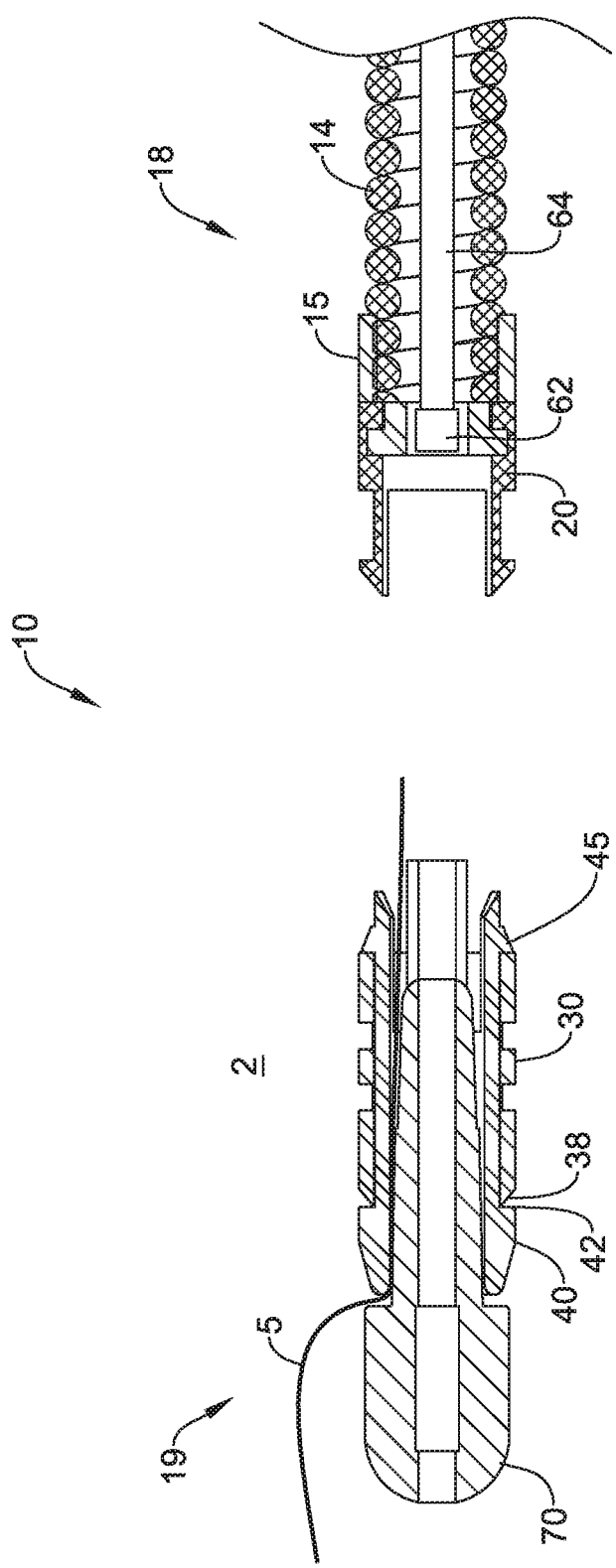
FIG. 6 is a side cross-sectional view of the medical device as shown in FIG. 1, in a fourth configuration, rotated 90 degrees from the view in FIG. 5.

When the prongs 45 reach the proximal end of the connection sleeve 30, the prongs 45 may engage this proximal end surface, placing the cinch sleeve in a final, locked position. In this locked position, the proximally facing shoulder surface 42 of the cinch sleeve 40 engages the distally facing end surface 38 of the connection sleeve 30, effectively locking the connection sleeve 30 between the prongs 45 and the proximally facing shoulder surface 42 of the cinch sleeve 40 in the fourth configuration, as shown in FIG. 6.

As the proximally facing shoulder surface 42 of the cinch sleeve 40 engages the distally facing end surface 38 of the connection sleeve 30, further proximal movement of the elongated inner shaft 64 may compress the distal region 62 and move the distal region 62 into and through the proximal section 78 of the cinch member lumen 76, allowing the elongated inner shaft 64 to move completely through and out of the cinch member lumen 76, disengaging the elongated inner shaft 64 from the cinch member 70. In a fourth stage of proximal longitudinal movement, the elongated inner shaft 64 moves through the cinch lumen 46, sleeve lumen 36, and coupler lumen 26, moving the device 100 into the fourth configuration as shown in FIG. 6. In some examples, the cap 15 or elongated shaft 14 may have a retention element such as an inner protrusion or reduced diameter region (not shown) that engages the distal region 62, preventing the distal region 62 from further proximal movement relative to the elongated shaft 14, holding the distal region 62 within the cap 15 or distal end of the elongated shaft 14.

The elongated shaft 14, cap 15 if present, and coupler 20 remain connected to one another, forming a shaft assembly 18. The shaft assembly 18 is released from the connection sleeve 30, and may be withdrawn from the body along with the elongated inner shaft 64. The cinch member 70, cinch sleeve 40, and connection sleeve 30, forming a cinch assembly 19, may be left in place adjacent the tissue 2 with the secured suture 5, as shown in FIG. 6. The suture 5 is embedded in the tissue 2 and secured adjacent the tissue 2 by the combination cinch member 70, cinch sleeve 40, and connection sleeve 30.

Figure 7:
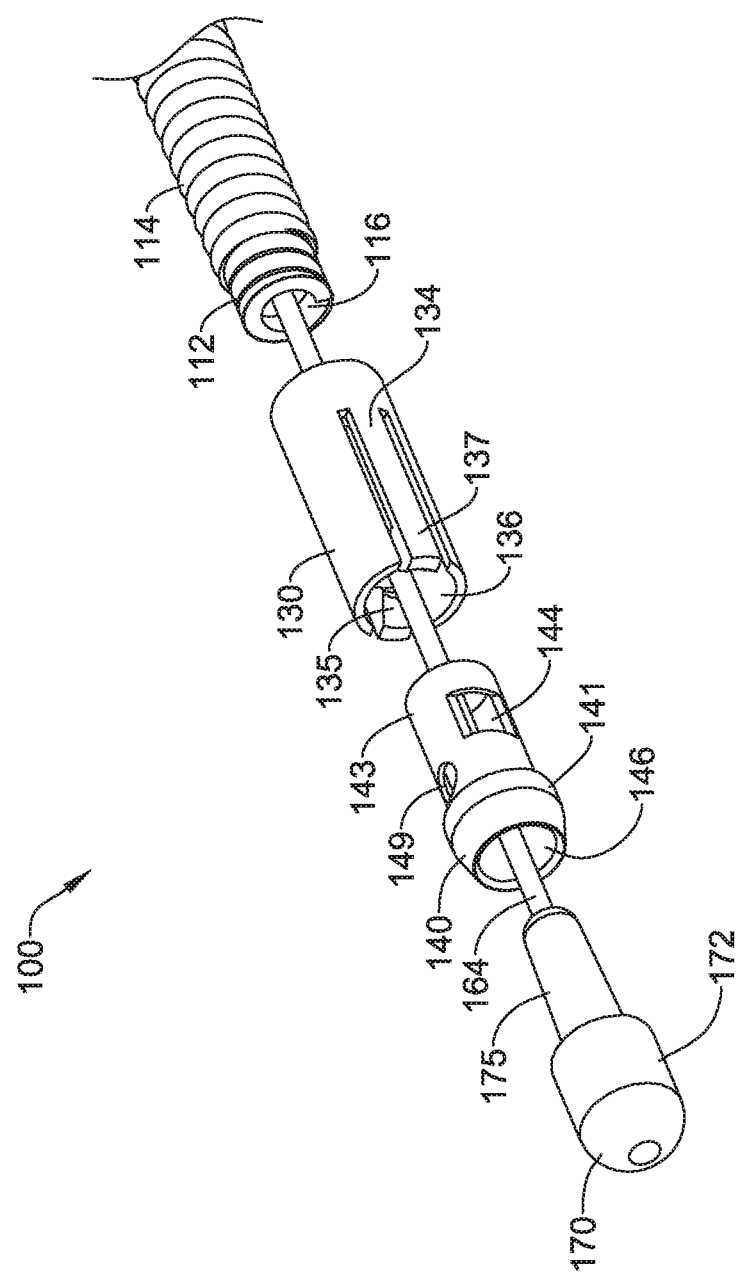
FIG. 7 is a perspective exploded view of a portion of another example medical device for applying a cinch to a suture.

FIGS. 7-12 illustrate another example medical device 100 for securing and cutting a suture. FIG. 7 shows a partial exploded view of a medical device 100 for applying a cinch to a suture. The medical device 100 may include an elongated shaft 114 having a shaft lumen 116, a connection sleeve 130 having a sleeve lumen 136, a cinch sleeve 140 having a cinch lumen 146, and a cinch member 170 having a cinch member lumen 176 (see FIG. 9). An elongated inner shaft 164 may extend through and be longitudinally movable through the shaft lumen 116, sleeve lumen 136, cinch lumen 146, and cinch member lumen 176. The elongated inner shaft 164 may be a solid wire, coil, or ribbon, or may be a generally tubular member defining a lumen along a part or the entire length thereof, or a combination of these structures.

The elongated shaft 114 may include and/or be made of an elongated tubular member defining the shaft lumen 116. In the embodiment shown, the elongated shaft 114 is a coiled tubular shaft, however, other configurations are contemplated. For example, the elongated shaft 114 may be a solid metallic or polymer tubular member, a tubular member including and/or made of and/or reinforced with a coil, braid and/or mesh material, or the like. Further, the elongated shaft 114 may include one or more slots and/or grooves and/or channels formed therein, for example, to enhance the flexibility characteristics thereof. The elongated shaft 114 may include or be made of one or more metals, polymers, and/or composite or layered or reinforced structures thereof, including any of those disclosed herein.

The distal end 112 of the elongated shaft 114 may be attached directly to the connection sleeve 130, for example with a threaded engagement, adhesive, weld, solder, or other suitable connection. The connection sleeve 130 may include at least one connector 134 configured to engage the cinch sleeve 140. In the example shown in FIGS. 7-12, the at least one connector 134 includes first and second opposing deflectable arms 137 each having an inwardly projecting prong 135 extending into the sleeve lumen 136. The prongs 135 may be disposed on distal ends of the deflectable arms 137 as shown in FIG. 7. In other examples, the prongs 135 may be disposed proximal of the distal ends of the deflectable arms 137.

The cinch sleeve 140 has an outer surface that may define a shoulder 141 and a proximal portion 143 extending proximal of the shoulder 141. The proximal portion 143 may include at least one proximal coupling member 144 configured to releasably engage the at least one connector 134 of the connection sleeve 130. In the example shown in FIGS. 7-12, the proximal coupling member 144 includes first and second opposing apertures 144 configured to releasably engage the prongs 135 on the deflectable arms 137. The cinch sleeve 140 may define an opening 149 in a sidewall of the proximal portion 143. The opening 149 provides an exit for a suture 5 disposed within the cinch lumen 146 of the cinch sleeve 140, as shown in FIG. 8.

Figure 9:
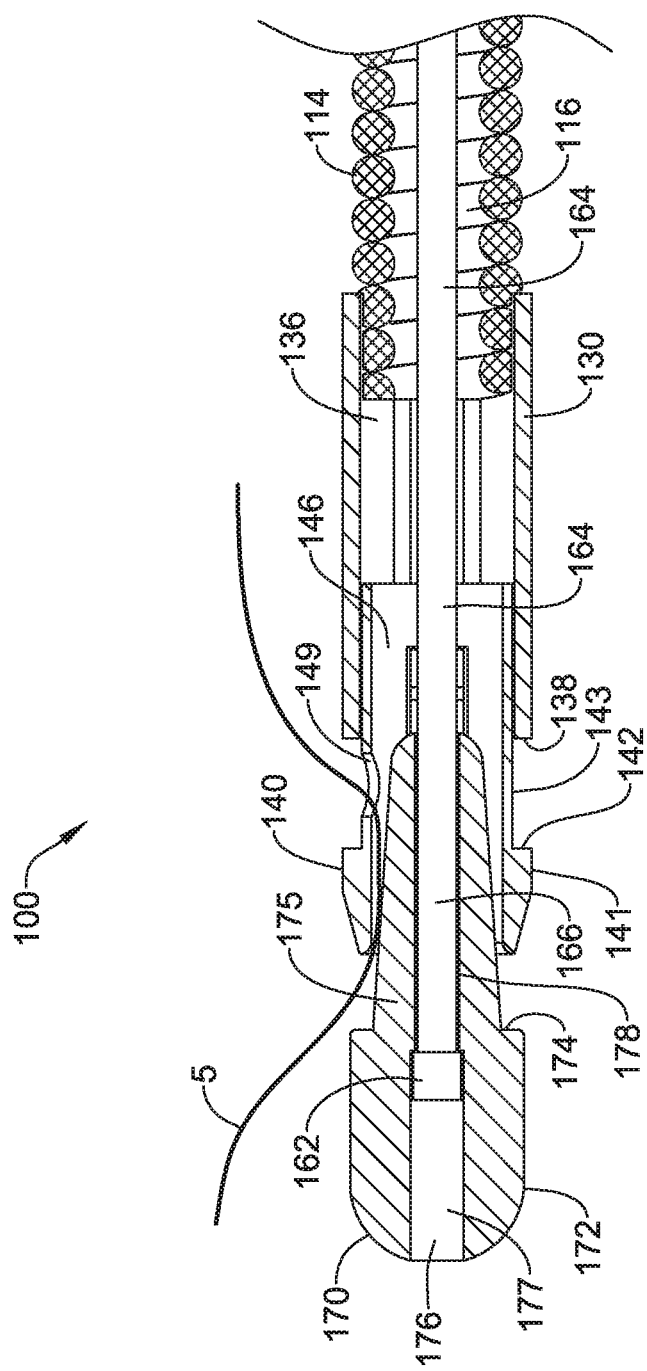
FIG. 9 is a side cross-sectional view of the medical device as shown in FIG. 7.

The shoulder 141 of the cinch sleeve 140 may have a proximally facing shoulder surface 142 and having a shoulder diameter greater than the diameter of the sleeve lumen 136, as shown in FIG. 9. In the embodiment shown, shoulder 141 is defined by a generally stepped portion having a rapid and/or stepped increase in outer diameter. However, in other embodiments, the outer surface of the cinch sleeve 140 may be tapered and/or angled gradually and/or in a stepwise fashion such that the outer diameter increases in size from the proximal portion 143 to the shoulder 141 in a distal direction in a more gradual manner, and the shoulder 141 may be more subtle. In such embodiments, the widened diameter portion and/or shoulder 141 may simply be defined by a first part along the outer surface that includes an outer diameter sized such that it cannot fit into the sleeve lumen 136. Such embodiments will still include a proximally facing shoulder surface 142, in that the angle and/or taper would still provide a surface that is facing in a proximal direction in a tapered and/or angled manner.

Figure 8:
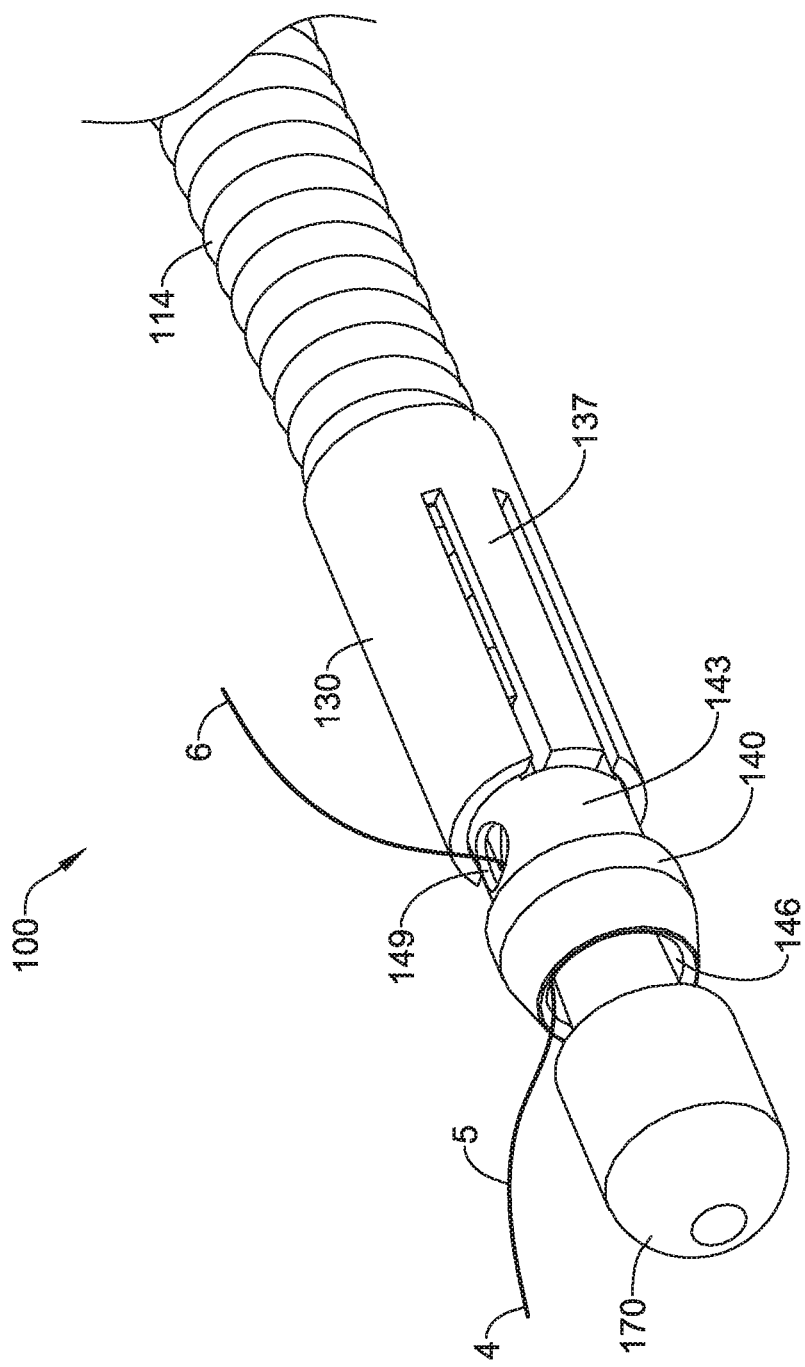
FIG. 8 is a perspective view of the medical device as shown in FIG. 7, in a first configuration.

In a first configuration, shown in FIGS. 8 and 9, the elongated shaft 114, connection sleeve 130, and cinch sleeve 140 are all connected, with the cinch member 170 extended distally away from the cinch sleeve 140. In this configuration, a suture 5 may be inserted into the distal end of the cinch sleeve 140, through a portion of the cinch lumen 146 and out through the opening 149.

The cinch member 170 may be configured to engage the cinch sleeve 140 in a friction fit to secure the suture 5. The cinch member 170 may include a distal head 172 with a diameter greater than the diameter of the cinch lumen 146, as shown in FIG. 9. The distal head 172 may have a proximally facing shoulder surface 174. The transition between the diameters of the distal head 172 and a proximal portion 175 may occur rapidly, defining a generally stepped shoulder portion having a rapid and/or stepped increase in outer diameter, as shown in FIG. 9. However, in other embodiments, the transition in diameters may be tapered and/or angled gradually and/or in a stepwise fashion such that the outer diameter increases in size in a distal direction in a more gradual manner, and a more subtle shoulder may be defined. In such embodiments, the widened diameter portion and/or shoulder may simply be defined by a distal head 172 that includes an outer diameter sized such that it cannot fit into the cinch lumen 146 of the cinch sleeve 140.

The cinch member 170 may have a proximal portion 175 configured to fit within the cinch lumen 146 in a friction fit. The cinch lumen 146 may have a tapered or constant inner diameter. The proximal portion 175 is configured and/or designed to mate with the cinch lumen 146 to trap and/or wedge a portion of a suture 5 therebetween. As such, the cinch member 170, in combination with the cinch sleeve 140, make up the "cinch" that will be applied to the suture. The cinch member 170 may have a cinch member lumen 176 extending at least partially therethrough. In the example shown in FIGS. 7-12, the cinch member lumen 176 extends completely through the cinch member 170, however, this is not necessary. In some examples, the cinch member lumen 176 may extend only through the proximal portion 175, with the distal head 172 being solid and devoid of any lumen. The cinch member lumen 176 may have a distal section 177 and a proximal section 178. The diameter of the distal section 177 may be larger than the diameter of the proximal section 178.

The elongated inner shaft 164 may include a distal region 162 and a proximal region 166. The distal region 162 and proximal region 166 may be a single monolithic piece, or the distal region 162 may be a separate element that is connected to the proximal region 166. The distal region 162 may be sized to engage the cinch member lumen 176. The diameter of the distal region 162 may be larger than the diameter of the proximal region 166. The diameter of the distal region 162 may be slightly larger than the proximal section 178 of the cinch member lumen 176 to provide an interference fit. In some examples, the distal region 162 may be compressible or deformable such that the application of a predetermined amount of proximal longitudinal force allows the interference fit to be overcome, thereby allowing the enlarged distal region 162 to be pulled through the narrower proximal section 178 of the cinch member lumen 176. In the first configuration, the distal region 162 of the elongated inner shaft 164 may be disposed within the distal section 177 of the cinch member lumen 176 with the proximal region 166 disposed within the proximal section 178 of the cinch member lumen 176, as shown in FIG. 9.

Figure 10:
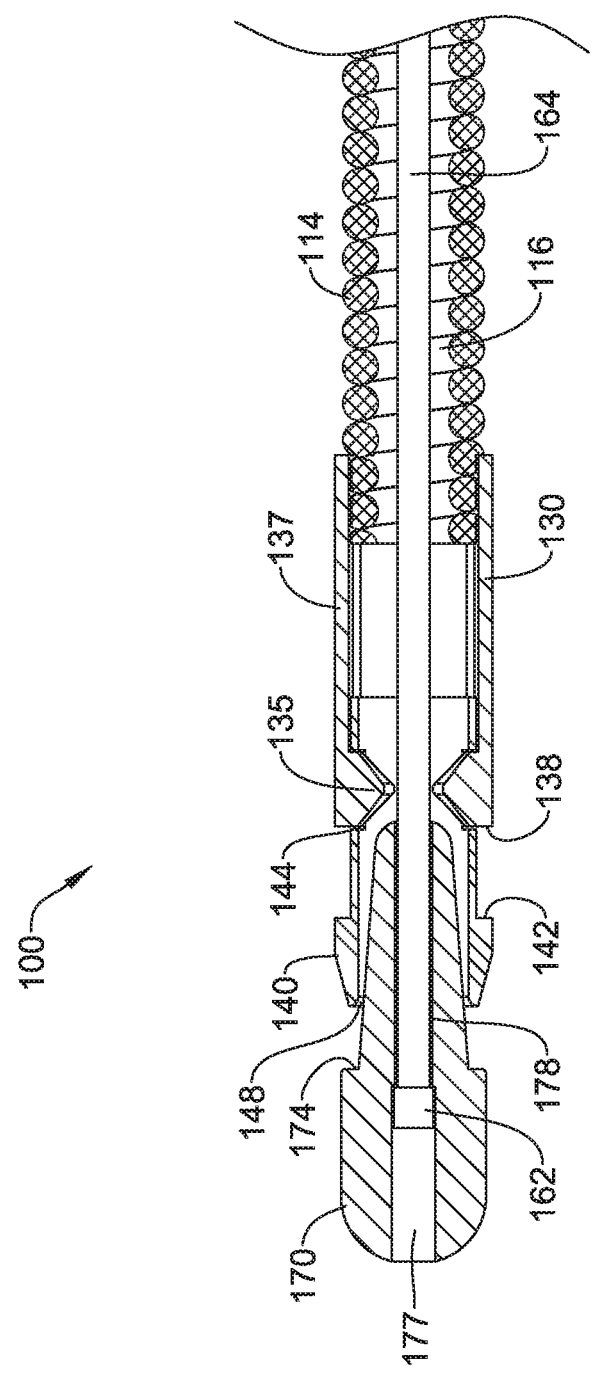
FIG. 10 is a side cross-sectional view of the medical device as shown in FIG. 7, taken 90 degrees from the view in FIG. 8.

FIGS. 8-12 illustrate the steps involved in securing and cutting a suture using the medical device 100. The medical device 100 is assembled into a deployment or first configuration shown in FIGS. 8-10. The elongated shaft 114, connection sleeve 130, and cinch sleeve 140 are all connected and the elongated inner shaft 164 is disposed within the cinch member lumen 176 and extends through the cinch lumen 146, sleeve lumen 136, and shaft lumen 116, with the cinch member 170 disposed distal of the cinch sleeve 140, as shown in FIGS. 8-10.

During assembly, as the connection sleeve 130 is moved over the proximal portion 143 of cinch sleeve 140 until the prongs 135 on the deflectable arms 137 are inserted into the apertures 144, thereby securing the cinch sleeve 140 to the connection sleeve 130, as shown in FIG. 10. The prongs 135 are configured such that proximal movement of the cinch member 170 deflects the prongs 135 outward, releasing them from the apertures 144.

In the first configuration, the cinch sleeve 140 may be in a distal position in which the proximal portion 143 of the cinch sleeve 140 is disposed within the sleeve lumen 136 and the prongs 135 are engaged with the apertures 144 of the cinch sleeve 140, and a gap is defined between the proximally facing shoulder surface 142 and a distal end surface 138 of the connection sleeve 130. The vertical distal end surface 138 also prevents proximal movement of the cinch sleeve 140 until the prongs 135 are raised far enough so that the angled surface of the prongs 135 contact the cinch sleeve 140. Likewise, the proximal vertical surface on the prongs 135 prevents distal movement of the cinch sleeve 140 until the prongs 135 are raised far enough to disengage from the apertures 144. The cinch member 170 is disposed either completely distal of the cinch sleeve 140 or only a part of the proximal portion 175 is inserted into the cinch lumen 146. This leaves the opening 149 exposed and provides space between the inner surface of the cinch lumen 146 and the proximal portion 175 for the suture 5 to be threaded through the cinch lumen 146 and out the opening 149, as shown in FIG. 9.

In the first configuration shown in FIGS. 8-10, the device 100 may be loaded with a suture 5 and be used to apply a cinch to the suture 5. For example, following a suturing procedure in which a first end 4 of the suture 5 is disposed within the tissue, the second, or free end 6 of the suture 5 may be loaded into and/or through the device 10. This may be done with or without using a tool or guide, such as a tubular guide, wire, loop, needle, or the like.

Figure 11:
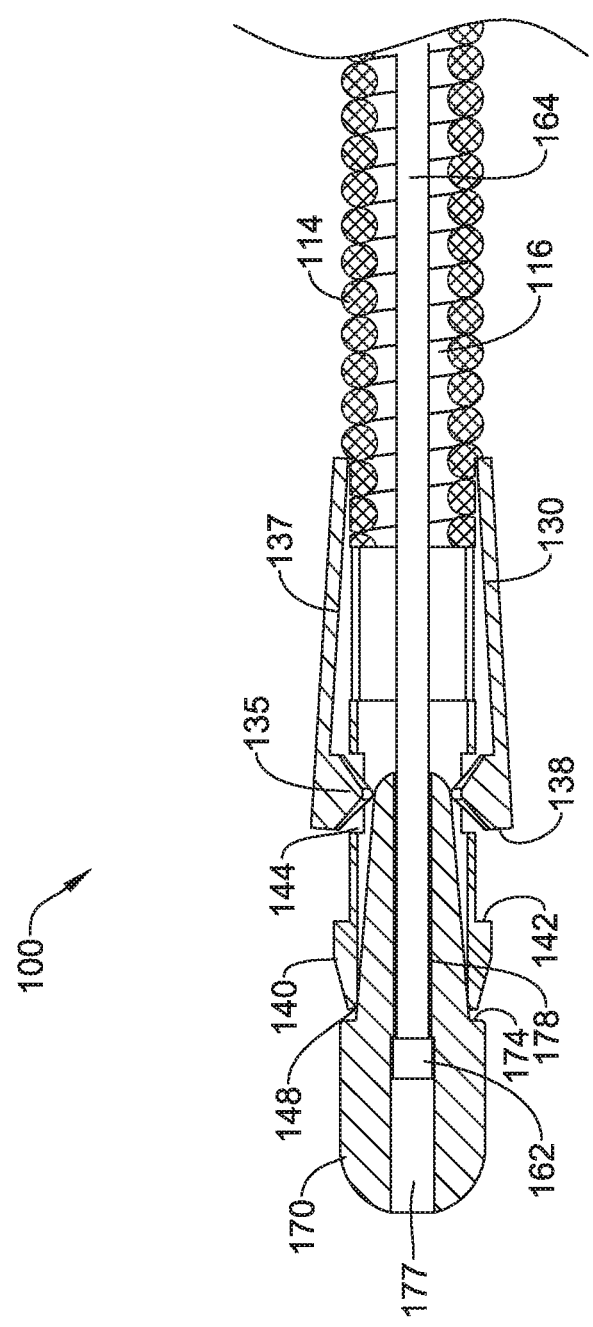
FIG. 11 is a side cross-sectional view of the medical device as shown in FIG. 7, in a second configuration.

Once the suture 5 is disposed within the cinch lumen 146 of the cinch sleeve 140, the suture 5 may be secured by moving the cinch member 170 into the cinch lumen 146 of the cinch sleeve 140. This may be achieved by pulling the inner shaft 164 proximally until the proximal portion 175 of the cinch member 170 engages the inner surface of the cinch sleeve 140, thereby compressing and securing the suture 5, as shown in FIG. 11. This second configuration results in the cinch member 170 displacing the prongs 135 and moving the deflectable arms 137 outward, allowing the connection sleeve 130 to be separated from the cinch sleeve 140.

The interference fit between the proximal portion 175 and the inner surface of the cinch lumen 146 secures the suture 5 even when there is a gap between the proximally facing shoulder surface 174 and the distal end 148 of the cinch sleeve 140. This gap may prevent crimping and possible damage to the suture as it bends at an approximately right angle. However, in other examples, the cinch member 170 may be pulled proximally until the proximally facing shoulder surface 174 engages the distal end 148 of the cinch sleeve 140, thereby providing an additional securement point. In such an example, the edges of the proximally facing shoulder surface 174 and the distal end 148 of the cinch sleeve 140 are generally smooth to prevent damage to the suture.

Movement of the cinch member 170 and cinch sleeve 140 may be achieved by engaging the distal region 162 of the elongated inner shaft 164 with the shoulder between the larger distal section 177 and the smaller proximal section 178 of the cinch member lumen 176. Proximal longitudinal movement of the elongated inner shaft 164 pulls the engaged cinch member 170 into the cinch lumen 146 of the cinch sleeve 140, thereby compressing and securing the suture 5 between the proximal portion 175 of the cinch member 170 and the inner surface of the proximal portion 143 of the cinch sleeve 140. Continued proximal movement of the elongated inner shaft 164 causes the distal end of the cinch member 170 to move the prongs 135 on the deflectable arms 137 out of the apertures 144 as the shoulder 141 of the cinch sleeve 140 meets the distal end surface 138 of the connection sleeve 130 in the second configuration, as shown in FIG. 11.

A cutting surface or shear edge may be defined on one or both of the distal end surface 138 of the connection sleeve 130 and the opening 149 in the cinch sleeve 140. Moving the cinch sleeve 140 into the connection sleeve 130 moves the opening 149 under the distal end surface 138, moving the suture 5 against the cutting surface and cutting the suture 5. Moving the device 100 from the first configuration shown in FIGS. 8-10 into the second configuration shown in FIG. 11 cinches the suture between the cinch member 170 and cinch sleeve 140 and cuts the suture 5.

Figure 12:
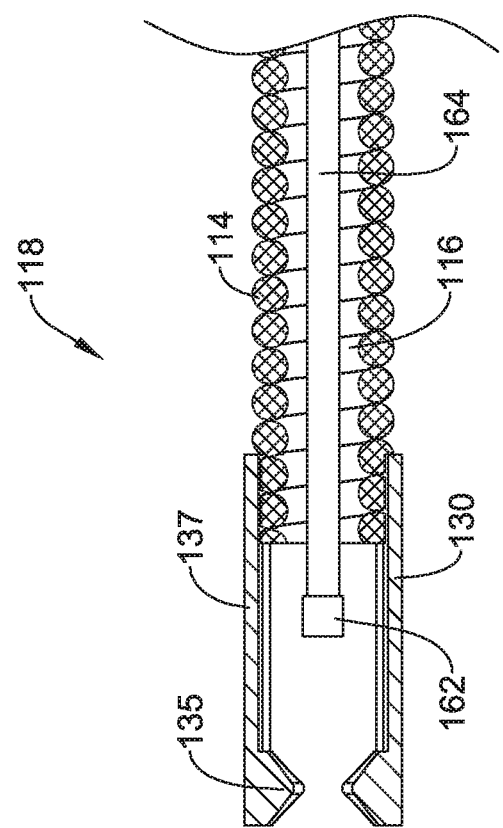
FIG. 12 is a side cross-sectional view of the medical device as shown in FIG. 7, in a third configuration.
Figure 12:
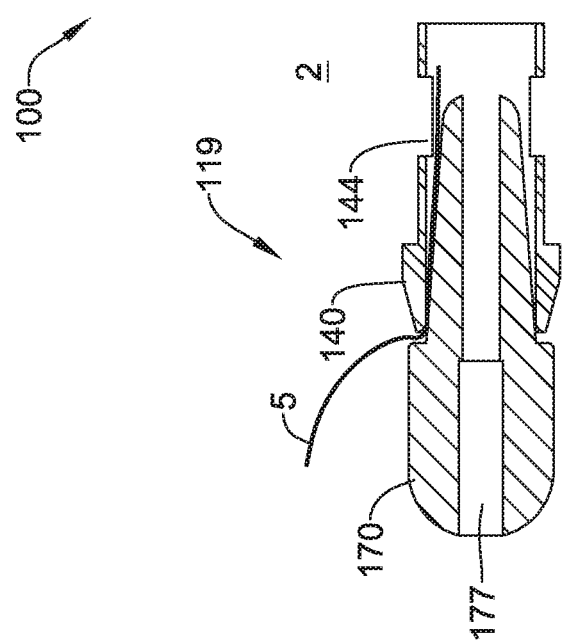

As the proximally facing shoulder surface 142 of the cinch sleeve 140 engages the distal end surface 138 of the connection sleeve 130 (FIG. 11), further proximal movement of the elongated inner shaft 164 may compress the distal region 162 and move the distal region 162 into and through the proximal section 178 of the cinch member lumen 176, allowing the elongated inner shaft 164 to move completely through and out of the cinch member lumen 176, disengaging the elongated inner shaft 164 from the cinch member 170, and allowing the elongated shaft 114 and connection sleeve 130 to be separated from the coupled cinch member 170 and cinch sleeve 140, resulting in the third configuration shown in FIG. 12. In some examples, the elongated shaft 114 or proximal region of the connection sleeve 130 may have a retention element such as an inner protrusion or reduced diameter region (not shown) that engages the distal region 162, preventing the distal region 162 from further proximal movement relative to the elongated shaft 114, holding the distal region 162 within distal end of the elongated shaft 114.

Figure 13:
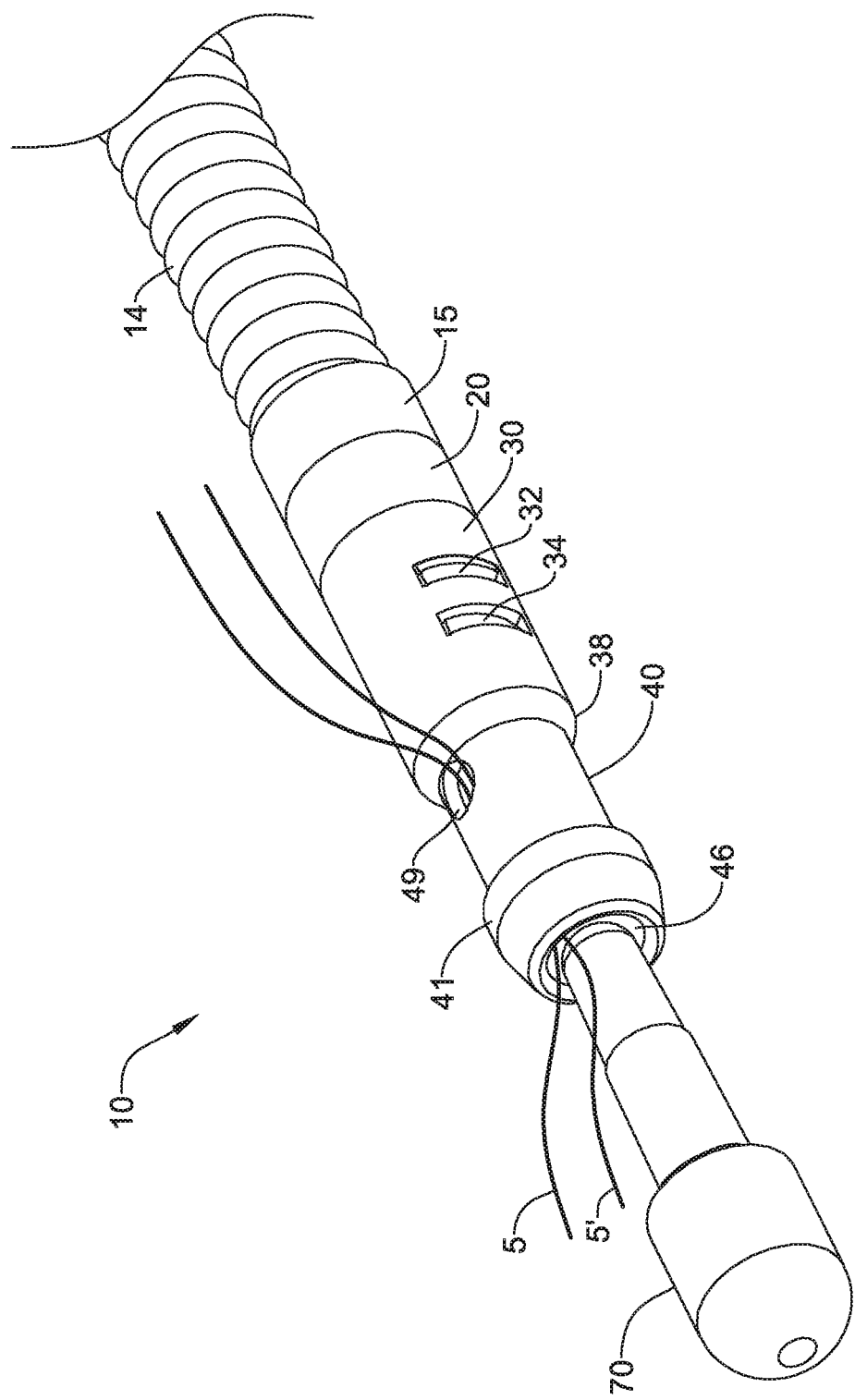
FIG. 13 is the medical device as shown in FIG. 2, with two sutures extending therethrough.

The elongated shaft 114 and attached connection sleeve 130 form a shaft assembly 118. The shaft assembly 118 is released from the cinch sleeve 140 and may be withdrawn from the body along with the elongated inner shaft 164. The cinch member 170 and cinch sleeve 140, forming a cinch assembly 119, may be left in place adjacent the tissue 2 with the secured suture 5, as shown in FIG. 12. The suture 5 is embedded in the tissue 2 and secured adjacent the tissue 2 by the combination cinch member 170 and cinch sleeve 140. In the above discussion, the various example medical devices are described as being used to secure "a" suture and the figures illustrate a single suture 5 being secured and cut with the devices. It will be understood that any of the medical devices described herein may be used to secure and cut any number of sutures including one, two, three, four, five, etc. FIG. 13 illustrates the device 10 shown in FIG. 2, but here with two sutures 5, 5' inserted into the distal end of the cinch sleeve 40 and out through the opening 49 in the sidewall.

The materials that can be used for the various components of the medical devices disclosed herein may include those commonly associated with medical devices. Any of the devices, members and/or components of members or devices disclosed herein may be made from a metal, metal alloy, polymer (some examples of which are disclosed below), a metal-polymer composite, ceramics, combinations thereof, and the like, or other suitable material or composites of materials. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments polymers can be blended with a liquid crystal polymer (LCP). For example, the mixture can contain up to about 6 percent LCP.

Some examples of suitable metals and metal alloys include stainless steel, such as 304V, 304L, 316LV, and 17-7 stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A medical device for applying a cinch to one or more sutures, the medical device comprising:
    an elongated shaft defining a shaft lumen;
    a connection sleeve having a sleeve lumen and first and second connectors;
    a cinch sleeve defining a cinch lumen and having a proximal portion with at least one proximal coupling member configured to releasably engage the second connector of the connection sleeve, the cinch sleeve having a distal position in which the proximal portion is disposed within the sleeve lumen and the at least one proximal coupling member is engaged with the second connector of the connection sleeve;
    a coupler connected to the elongated shaft, the coupler having a coupler lumen and a distal end of the coupler defining a distal coupling member, the distal coupling member being configured to releasably engage the first connector of the connection sleeve;
    a cinch member defining a cinch member lumen, the cinch member including at least a proximal segment configured to fit within the cinch lumen; and
    an elongated inner shaft extending through and longitudinally movable within the shaft lumen, the sleeve lumen, the cinch lumen, and the cinch member lumen.

2. The medical device of claim 1, wherein the sleeve lumen has a sleeve lumen diameter, the cinch sleeve having an outer surface defining a shoulder, the shoulder having a proximally facing shoulder surface and having a shoulder diameter greater than the sleeve lumen diameter, wherein the proximal portion of the cinch sleeve extends proximal of the shoulder.

3. The medical device of claim 2, wherein when the cinch sleeve is in the distal position, a gap is defined between the proximally facing shoulder surface and a distally facing end surface of the connection sleeve.

4. The medical device of claim 3, further comprising an opening through the outer surface of the cinch sleeve into the cinch lumen, and at least one suture cutting element disposed on one or both of the connection sleeve and the opening, and wherein proximal movement of the cinch sleeve from the distal position to a proximal position engages the at least one suture cutting element for cutting one or more sutures extending through the opening.

5. The medical device of claim 4, wherein when the cinch sleeve moves toward the proximal position, the at least one proximal coupling member disengages from the second connector of the connection sleeve and moves proximally, releasing the distal coupling member of the coupler from the first connector of the connection sleeve.

6. The medical device of claim 1, wherein a distal end section of the elongated inner shaft is configured to releasably engage the cinch member lumen, wherein proximal longitudinal movement of the elongated inner shaft moves the cinch member from a first configuration in which at least a part of the cinch member is spaced apart from a distal end of the cinch sleeve, to a second configuration in which the cinch member engages the cinch lumen.

7. The medical device of claim 6, wherein from the second configuration, further proximal longitudinal movement of the elongated inner shaft moves the cinch sleeve proximally such that the at least one proximal coupling member is engaged with the first connector of the connection sleeve, and the distal coupling member of the coupler is disengaged from the connection sleeve, resulting in a third configuration.

8. The medical device of claim 7, wherein further proximal longitudinal movement of the elongated inner shaft moves the coupled cinch member and cinch sleeve from the third configuration to a fourth configuration in which a cinch assembly including the cinch member, cinch sleeve, and connection sleeve is separated from a shaft assembly including the elongated shaft and the coupler.

9. The medical device of claim 8, wherein the cinch member lumen has a distal section and a proximal section, wherein a diameter of the distal section is larger than a diameter of the proximal section, wherein the elongated inner shaft includes a distal region having a diameter larger than the diameter of the proximal section of the cinch member lumen, wherein the distal region is compressible such that application of a predetermined amount of proximal longitudinal force compresses the distal region, allowing it to move into the proximal section of the cinch member lumen.

10. The medical device of claim 1, wherein the first and second connectors are first and second apertures, and the distal coupling member and the at least one proximal coupling members include proximal and distal prongs configured to removably engage the first and second apertures.

11. The medical device of claim 1, wherein the sleeve lumen has a sleeve lumen diameter, the cinch sleeve having an outer surface defining a shoulder, the shoulder having a proximally facing shoulder surface and having a shoulder diameter greater than the sleeve lumen diameter, wherein the proximal portion of the cinch sleeve extends proximal of the shoulder, wherein when the cinch sleeve is in the distal position, a gap is defined between the proximally facing shoulder surface and a distally facing end surface of the connection sleeve.

12. The medical device of claim 11, further comprising an opening through the outer surface of the cinch sleeve into the cinch lumen, and at least one suture cutting element disposed on one or both of the connection sleeve and the opening, and wherein proximal movement of the cinch sleeve from the distal position to a proximal position engages the at least one suture cutting element for cutting one or more sutures extending through the opening.

13. The medical device of claim 12, wherein when the cinch sleeve moves from the distal position to the proximal position, the at least one proximal coupling member disengages from the second connector of the connection sleeve, releasing the connection sleeve from the cinch sleeve.

14. The medical device of claim 13, wherein a distal end section of the elongated inner shaft is configured to releasably engage the cinch member lumen, wherein proximal longitudinal movement of the elongated inner shaft moves the cinch member from a first configuration in which at least a part of the cinch member is spaced apart from a distal end of the cinch sleeve, to a second configuration in which the cinch member engages the cinch lumen.

15. The medical device of claim 14, wherein as the cinch member moves from the first configuration to the second configuration, a distal end of the cinch member moves the at least one proximal coupling member out of engagement with the second connector on the connection sleeve.

16. The medical device of claim 15, wherein further proximal longitudinal movement of the elongated inner shaft moves the coupled cinch member and cinch sleeve from the second configuration to a third configuration in which a cinch assembly including the cinch member, cinch sleeve, and connection sleeve is separated from a shaft assembly including the elongated shaft and the coupler.

\* \* \* \* \*